United States Patent [19]

Levrant

[11] Patent Number: 5,046,605
[45] Date of Patent: Sep. 10, 1991

[54] CONTACT LENS CONTAINER HOLDER

[75] Inventor: Paul Levrant, London, United Kingdom

[73] Assignee: Boulevard Products Ltd., Great Britain

[21] Appl. No.: 485,107

[22] Filed: Feb. 23, 1990

[51] Int. Cl.⁵ .............................................. A45C 11/04
[52] U.S. Cl. .................................... 206/5.1; 206/459; 206/534; 116/309
[58] Field of Search ................ 206/5.1, 459, 486, 490, 206/534; 116/309, 317, 330; 215/365, 366

[56] References Cited

U.S. PATENT DOCUMENTS

| | | | |
|---|---|---|---|
| 2,706,464 | 4/1955 | North | 206/5.3 |
| 3,052,246 | 9/1962 | Beard | 206/5.1 |
| 3,460,508 | 8/1969 | Baxter | 116/317 |
| 3,818,858 | 6/1974 | Kramer et al. | 116/309 |
| 3,960,713 | 6/1976 | Carey | 206/459 |
| 3,996,879 | 12/1976 | Walton | 206/534 |
| 4,171,717 | 10/1979 | Fleming | 116/317 |
| 4,345,541 | 8/1982 | Villa-Real | 206/459 |
| 4,405,045 | 9/1983 | Villa-Real | 206/459 |
| 4,444,307 | 4/1984 | Jermyn | 206/5.1 |
| 4,528,933 | 7/1985 | Allen | 206/534 |
| 4,548,157 | 10/1985 | Hevoyan | 206/459 |
| 4,616,750 | 10/1986 | Nouwen | 206/459 |
| 4,877,119 | 10/1989 | Hosking | 116/317 |
| 4,909,382 | 3/1990 | Cuppari | 206/5.1 |

Primary Examiner—David T. Fidei
Attorney, Agent, or Firm—Jones, Day, Reavis & Pogue

[57] ABSTRACT

A contact lens container holder consists of a base member 1 formed with a well 2 which is sized to receive a contact lens container 3. The base member 1 has a skirt 4 in which are formed a plurality of rectangular apertures 5. Behind the skirt is a rotatable member having segments of different colors red and green with means for rotating it so that if the contact lens container contains for example peroxide the color red will be seen through the apertures 5 whereas if it contains neutralizing solution the rotatable member is reset to show green through the apertures 5.

9 Claims, 1 Drawing Sheet

CONTACT LENS CONTAINER HOLDER

BACKGROUND OF THE INVENTION

This invention relates to holders for contact lens containers, particularly for lens which are cleaned and sterilised by a two stage process. In this process the lenses are first soaked in a hydrogen peroxide solution to achieve a sterile state and are then soaked for a further period of time in a neutralising solution which removes the hydrogen peroxide from the lenses, making them allowable for insertion in the eye.

The sterilising process is usually carried out in the same container. Once the hydrogen peroxide has been present for a sufficient time to have the desired effect, it is tipped away and the container is filled with neutralising solution. Herein lies a danger, because if the user forgets the neutralising stage and inserts into his or her eye a lens impregnated and coated with hydrogen peroxide a severe trauma ensues, generating considerable pain and sometimes requiring medical assistance to remove the lens from the eye.

OBJECT OF THE INVENTION

The object of the invention is to provide a holder for the container which is adapted to give a visual warning when only the first of a multi-stage sterilising process has been completed.

SUMMARY OF THE INVENTION

According to the invention there is provided a contact lens container holder comprising a base formed with a well adapted to receive and stably support the container and provided with manually actuatable indicator means adapted to display at least two differentiable visual indications of the state of the contents of the container.

Thus when the container is filled with peroxide solution the indicator means can be set to display a for example red visual indication. This will warn the user not to insert the lenses into his eye without first completing the second stage. When the neutralising solution is added to the container the indicator means can be set to display a for example green visual indication which means that the user can feel free to insert the lenses into his or her eye. In other words, the invention removes the necessity for the user to remember whether he or she did in fact complete the second stage of the sterilising process.

Features of the invention which are particularly preferred although not necessarily essential are as follows:

(1) The indicator means consists of at least one aperture formed in the base behind which is selectively movable a member having at least two differently coloured regions thereon a respective one of which is visible through the aperture in two different positions of the member.

(2) A plurality of such apertures are provided said member having differently coloured regions corresponding to each aperture.

(3) The base is formed with a skirt and the or each aperture is formed in the skirt.

(4) The movable member is rotatable about an axis coaxial with the well.

(5) The movable member is journalled in a bore formed in the base of the well.

(6) The movable member is provided with means for detenting it in each of two positions.

(7) The movable member is provided with a protruding tag whereby it may be moved by finger pressure between its said positions.

(8) The movable member is provided with one or more digit receiving indentations on its underside to facilitate manual rotation.

In order that the invention may be readily understood an embodiment thereof will be described by way of example with reference to the accompanying drawings:

DESCRIPTION OF THE PREFERRED EMBODIMENTS view of the contact lens

Figure 1:
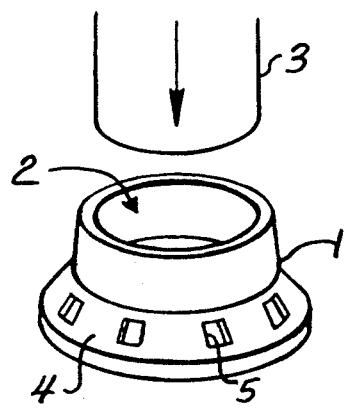
FIG. 1 is a perspective view of a contact lens container holder according to the invention.
Figure 2:
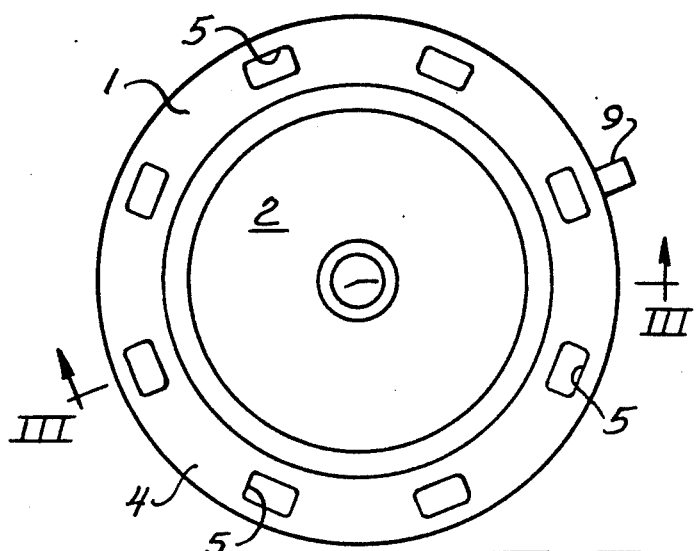
FIG. 2 is a plan view of the holder of FIG. 1.
Figure 3:
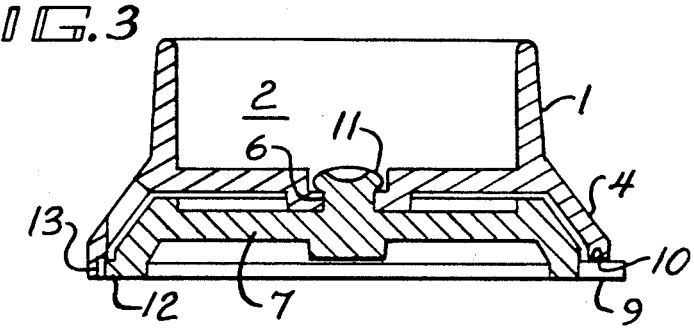
FIG. 3 is a cross-section along lines III—III of FIG. 2.
Figure 4:
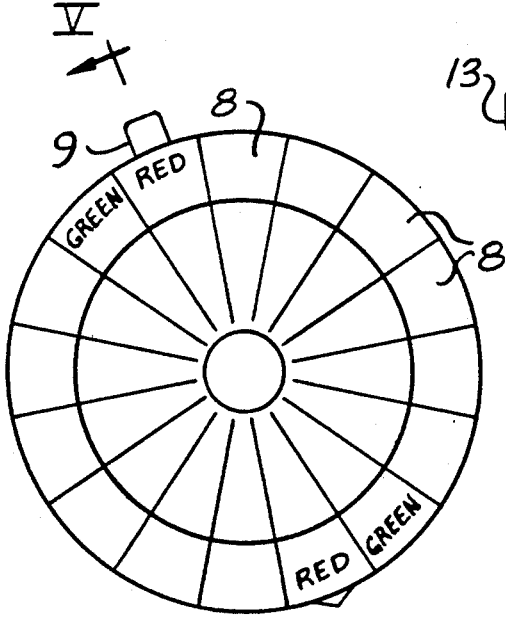
FIG. 4 is a plan view of the rotatable element.
Figure 5:
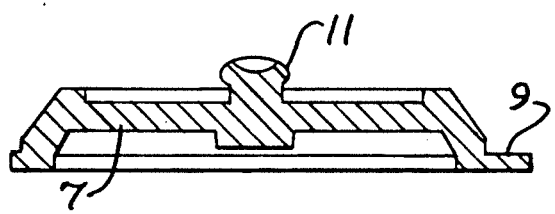
FIG. 5 is a cross-section along the line V—V of FIG. 4.

FIG. 1 shows an overall view of the contact lens container holder which comprises a base member 1 formed with a well 2 which is sized to receive a contact lens container 3, only part of which is shown.

The base 1 is formed with a skirt 4 in which are formed a plurality of rectangular apertures 5.

Journalled into a bore 6 formed in the base of the well 2 is a central, axially projecting hub 11 of a rotatable disc-shaped member 7 which is formed at its periphery (e.g. by printing) with segments 8 of different alternate colours red and green, and a protruding tag 9 which is adapted to protrude out of slot 10 formed in the skirt 4 and enable the rotatable member 7 to be moved between two different angular positions in each of which either the red segments or green segments 8 are visible through aperture 5.

Thus in use, when the contact lens wearer is soaking the lenses in a peroxide solution in container 3, he or she can place the container into the well for stable support and by use of the tag 9 set the red segments 8 visible through the aperture 5. The visual indication of red is a warning to the user that the lenses should not be inserted into the eye.

When the peroxide solution is removed and neutralising solution added to the container, the movable member can be reset so that the green segments show through the apertures 5, which is an indication to the user that the lenses can be inserted into the eye.

The rotatable member 7 is formed on its periphery at a position circumferentially spaced from the tag 9 with a small radially projecting detent member 12 for detenting in either one of a pair of detent recesses 13 formed on the inside of the skirt 4 at positions spaced circumferentially so as to allow the rotatable member to be selectively detented in its two different angular positions.

Figure 6:
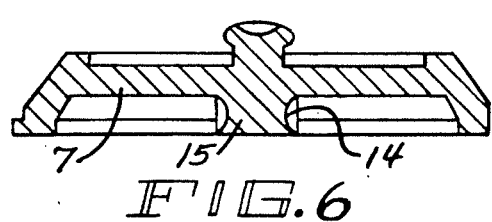
FIG. 6 is a cross-section of an alternative form of rotatable element.

In the embodiment illustrated in FIG. 6, the tag 9 is replaced by two digit-receiving indentations 14 on opposite sides of a central downward extension 15 of the hub 11, as a manual means to facilitate manual rotation of the member 7.

What is claimed is:

1. A holder for retaining a contact lens container comprising:

retaining means having at least one wall defining a well for receiving a contact lens container wherein the retaining means defines an aperture;

first and second visual indications disposed on said retaining means, corresponding to first and second states respectively of the contents of a contact lens container, the first and second visual indications comprising a first region and a second region, the first and second regions being of different colors; and manually actuable means for switching between said first and second visual indications comprising a display member bearing the first and second regions, the display member being movable between a first position in which the first region is visible through the aperture in the retaining means and a second position in which the second region is visible through the aperture.

2. The holder according to claim 1 in which the display member is provided with means for detenting it in each of two positions.

3. The holder according to claim 1 in which the display member further comprises a protruding tag whereby the display member may be moved by finger pressure between the first and second positions.

4. The holder of claim 1 in which the display member further comprises an underside containing one or more digit receiving indentations to facilitate manual rotation.

5. The holder of claim 1 wherein the retaining means defines a plurality of apertures, and the first and second regions comprise a plurality of first regions and a plurality of second regions respectively, and wherein the plurality of first regions are visible through the apertures in the first position and the plurality of second regions are visible through the apertures in the second position.

6. The holder of claim 1 wherein the retaining means further comprises a skirt attached to the wall defining the well, in which the aperture is formed.

7. The holder of claim 5 wherein the retaining means further comprises a skirt attached to the wall defining the well, in which each aperture is formed.

8. The holder of claim 1 wherein the well has an axis and wherein the display member is rotatable about an axis coaxial with the axis of the well.

9. The holder of claim 7 wherein the retaining means further comprises a base member having a bore formed therein and wherein the display member is journalled in said bore.

* * * * *